United States Patent [19]

Berg

[11] Patent Number: 5,423,954
[45] Date of Patent: Jun. 13, 1995

[54] SEPARATION OF 2-BUTANONE FROM ISOPROPANOL BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 370,391

[22] Filed: Jan. 9, 1995

[51] Int. Cl.⁶ .................... B01D 3/36; C07C 31/10; C07C 45/84
[52] U.S. Cl. .................................... 203/60; 203/63; 203/70; 568/410; 568/913
[58] Field of Search ................ 203/60, 63, 70; 568/410, 913

[56] References Cited

U.S. PATENT DOCUMENTS

| | | | |
|---|---|---|---|
| 2,481,211 | 9/1949 | Fuqua | 203/63 |
| 2,500,329 | 3/1950 | Steitz | 203/70 |
| 2,528,761 | 11/1950 | Lake et al. | 203/69 |
| 2,575,285 | 11/1951 | Carlson et al. | 203/63 |
| 2,617,757 | 11/1952 | Michael | 203/69 |

*Primary Examiner*—Wilbur Bascomb, Jr.

[57] ABSTRACT

2-Butanone is difficult to separate from isopropanol by conventional distillation or rectification because of the proximity of their boiling points. 2-Butanone can be readily separated from isopropanol by azeotropic distillation. Effective agents are 3-methyl pentane, methyl t-amyl ether and acetonitrile.

2 Claims, No Drawings

SEPARATION OF 2-BUTANONE FROM ISOPROPANOL BY AZEOTROPIC DISTILLATION

FIELD OF THE INVENTION

This invention relates to a method for separating 2-butanone from isopropanol using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 2 shows that a relative volatility of at least 1.2 is required to get an effective separation by rectification

TABLE 1

Effect of Relative Volatility on Theoretical Stage Requirements.

| Separation Purity, Both Products (Mole Fraction) | Relative Volatility | | | | | | | |
|---|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 32 | 40 | 33 | 15 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 15 | 10 | 6 |
| 0.95 | 296 | 61 | 31 | 21 | 16 | 24 | 8 | 4 |
| 0.90 | 221 | 45 | 23 | 16 | 12 | 10 | 5 | 3 |

There are a number of commercial processes that produce complex mixtures of oxygenated compounds, e.g. the Fischer-Tropach process. Two of the commonest oxygenated compounds usually present are 2-butanon B.P.=80° C. and isopropanol, B.P.=82° C. The relative volatility between these two is 1.35 which makes it difficult to separate them by conventional rectification. Azeotropic distillation would be an attractive method of effecting the separation of 2-butanone from isopropanol if agents can be found the (1) will create a large apparent relative volatility between 2-butanone and isopropanol and (2) are easy to recover from the 2-butanone. Table 2 shows the relative volatility required to obtain 99% purity.

TABLE 2

Theoretical and Actual Plates Required vs. Relative Volatility for 2-Butanone - Isopropanol Separation

| Relative Volatility | Theoretical Plates Required At Total Reflux, 99% Purity | Actual Plates Required 75% Efficiency |
|---|---|---|
| 1.35 | 31 | 42 |
| 1.7 | 17 | 23 |
| 2.3 | 11 | 15 |

OBJECTIVE OF THE INVENTION

The object of this invention is to provide a process or method of azeotropic distillation that will enhance the relative volatility of 2-butanone from isopropanol in their separation in a rectification column. It is a further object of this invention to identify organic compounds which in addition to the above constraints, are stable, can be separated from 2-butanone and recycled to the azeotrope column with little decomposition.

SUMMARY OF THE INVENTION

The objects of this invention are to provide a process for separating 2-butanone from isopropanol which entails the use of certain organic compounds as the agent in azeotropic distillation.

TABLE 3

Effective Azeotropic Distillation Agents For Separating 2-Butanone From-Isopropanol

| Compounds | Relative Volatility |
|---|---|
| None | 1.35 |
| 3-Methyl Pentane | 2.3 |
| 2,2-Dimethyl butane | 1.6 |
| 2,3-Dimethyl butane | 1.5 |
| Methyl formate | 1.55 |
| Methyl t-butyl ether | 1.5 |
| Methyl t-amyl ether | 1.7* |
| Ethyl ether | 1.55 |
| Acetonitrile | 1.65** |

*Data obtained in multiplate column
**Brings 2-butanone out as overhead

DETAILED DESCRIPTION OF THE INVENTION

I have discovered that certain organic compounds will greatly improve the relative volatility of 2-butanone to isopropanol and permit the separation of 2-butanone from isopropanol by rectification when employed as the agent in azeotropic distillation. Table 3 lists the compounds that I have found to be effective. They are 3-methyl pentane, 2,2-dimethyl butane, 2,3-dimethyl butane, methyl formate, methyl t-butyl ether, methyl t-amyl ether, ethyl ether and acetonitrile.

THE USEFULNESS OF THE INVENTION

The usefulness or utility of this invention can be demonstrated by referring to the data presented in Tables 2 and 3. All of the successful agents show that 2-butanone can be separated from isopropanol by means of azeotropic distillation in a rectification column and that the ease of separation as measured by relative volatility is considerable.

WORKING EXAMPLES

Example 1: Thirty grams of isopropanol, ten grams of 2-butanone and 30 grams of 3-methyl pentane were charged to a vapor-liquid equilibrium still and refluxed for three hours. Analysis indicated a vapor composition of 39.2% 2-butanone, 60.8% isopropanol; a liquid composition of 21.3% 2-butanone, 78.7% isopropanol. This is a relative volatility of 2.3.

Example 2: Ten grams of isopropanol, 20 grams of 2-butanone and 30 grams of acetonitrile were charged to a vapor-liquid equilibrium still and refluxed for three hours. Analysis indicated a vapor composition of 41.5% isopropanol, 58.5% 2-butanone; a liquid composition of 29.6% isopropanol, 70.4% 2-butanone. This is a relative volatility of isopropanol to 2-butanol of 1.65.

Example 3: Fifty grams of 2-butanone, 50 grams of isopropanol and 100 grams of methyl t-amyl ether were placed in the stillpot of a 5.6 theoretical plate glass perforated plate rectification column and refluxed for four hours. The overhead composition was 44.6% 2-butanone, 55.4% isopropanol; the bottoms composition was 3.9% 2-butanone, 96.1% isopropanol. This is a relative volatility of 1.7.

I claim:

1. A method for recovering 2-butanone from a mixture of 2-butanone and isopropanol which comprises distilling a mixture of 2-butanone and isopropanol in the presence of an azeotrope forming agent, recovering the 2-butanone and the azeotrope forming agent as overhead product and obtaining the isopropanol as bottoms product, wherein said azeotrope forming agent consists of one material selected from the group consisting of 3-methyl pentane, 2,2-dimethyl butane, 2,3-dimethyl butane, methyl formate, methyl t-butyl ether, methyl t-amyl ether and ethyl ether.

2. A method for recovering isopropanol from a mixture of isopropanol and 2-butanone which comprises distilling a mixture of isopropanol and 2-butanone in the presence of an azeotrope forming agent, recovering the isopropanol and the azeotrope forming agent as overhead product and obtaining the 2-butanone as bottoms product, wherein said azeotrope forming agent is acetonitrile.

* * * * *